United States Patent [19]

Cleveland

[11] 4,247,468

[45] Jan. 27, 1981

[54] LACTONE PREPARATION BY CYCLIZATION

[75] Inventor: James D. Cleveland, Albany, Calif.

[73] Assignee: Chevron Research Company, San Francisco, Calif.

[21] Appl. No.: 45,369

[22] Filed: Jun. 4, 1979

Related U.S. Application Data

[63] Continuation-in-part of Ser. No. 891,431, Mar. 29, 1978, abandoned.

[51] Int. Cl.³ .......................................... C07D 307/32
[52] U.S. Cl. ................................................. 260/343.6
[58] Field of Search ..................................... 260/343.6

[56] References Cited

U.S. PATENT DOCUMENTS

| 2,530,348 | 11/1950 | Britton et al. | 260/343.6 |
| 3,933,860 | 1/1976 | Chan | 260/343.6 |

OTHER PUBLICATIONS

J. E. Litvak et al., Jour. Am. Chem. Soc., vol. 67, (1945), pp. 2218–2220.

H. Plieninger, Chemische Berichte, vol. 83, (1950), pp. 265–268.

*Primary Examiner*—Norma S. Milestone
*Attorney, Agent, or Firm*—J. A. Buchanan, Jr.; D. A. Newell; T. G. DeJonghe

[57] ABSTRACT

A process for cyclizing 2,4-dibromobutyric acid (DBBA) to alpha-bromo-gamma-butyrolactone (BBL) which comprises contacting the dibromobutyric acid with a base at a temperature between 20° C. and 100° C. and a pH below about 4.0.

9 Claims, No Drawings

LACTONE PREPARATION BY CYCLIZATION

This application is a continuation-in-part of application Ser. No. 891,431, filed Mar. 29, 1978 and now abandoned.

BACKGROUND OF THE INVENTION

The present invention is concerned with the preparation of alpha-bromo-gamma-butyrolactone which can be used in the preparation of various useful chemicals such as the fungicides disclosed in Chan, U.S. Pat. No. 3,933,860.

H. Plieninger, Chemische Berichte, V. 83, No. 3, pp. 265-268 (1950) discusses the cleavage of gamma-lactones with alkyl mercaptides. Plieninger discloses preparation of 2,4-dibromobutyric acid bromide and its conversion into 2,4-dibromo-butyric acid, which in turn is converted into alpha-bromo-gamma-butyrolactone. In the Plieninger reaction sequence, 2 mols of bromine are added to 1 mol of butyrolactone in the presence of 0.4 mol phosphorus catalyst at a temperature of 25° to 80° C. to obtain the dibromobutyric acid bromide. Then this acid bromide is mixed with water to obtain the dibromobutyric acid. Finally, the dibromobutyric acid is refluxed with water to obtain alphabromo-butyrolactone.

Livak et al, JACS Vol. 67, p. 2218 (1945), "Synthesis of DL Methionine", discusses the reaction of 1 mol of gamma-butyrolactone with about 1 mol of bromine in the presence of 0.02 mol phosphorus tribromide at a temperature of 100°-130° C. and a reaction time of about 14 hours, followed by distillation under vacuum to obtain alpha-bromo-gamma-butyrolactone. Livak et al mention that the alpha-gamma-dibromobutyric acid obtained from the bromination can be converted to alpha-bromo-gamma-butyrolactone "on distillation or treatment with cold alkali".

SUMMARY OF THE INVENTION

According to the present invention, a process is provided for cyclizing 2,4-dibromobutyric acid to alpha-bromo-gamma-butyrolactone which comprises contacting the dibromobutyric acid with base at a temperature between 20° C. and 100° C. and a pH below about 4.0.

I have found that temperatures of 30° to 80°, especially 45° to 65° C., are especially advantageous in that both fast reaction rate and high cyclization yields are obtained compared to the use of cold temperatures or temperatures even as high as 25° C. Also, I have found that controlling the amount of base used to maintain a pH no higher than about 4 is important in achieving consistent high yields of the alpha-bromo-gamma-butyrolactone. Thus, controlling the base to yield a pH of between 0.1 and 4.0, more preferably between 0.5 and 4.0, and most preferably between 0.5 and 2.5 for the cyclization is especially desired in the process of the present invention.

According to another embodiment of the invention, an overall process is provided for producing alpha-bromo-gamma-butyrolactone which comprises feeding to a reaction zone gamma-butyrolactone, bromine and a phosphorus halide catalyst in a mol ratio of about 1 mol of the lactone, 0.5 to 1.2 mols of the bromine, and 0.01 to 0.10 mol of the catalyst; contacting the lactone, bromine and phosphorus halide catalyst in the reaction zone at a temperature between 75° and 180° C. to thereby form 2,4-dibromobutyric acid; and cyclizing the dibromobutyric acid to alpha-bromo-gamma-butyrolactone by contacting the acid with a base, preferably alkali metal carbonate, at a temperature between 20° and 90° C., preferably between about 45° and 65° C. and at a pH between 0.5 and 4.0. Preferably the alkali metal carbonate is sodium carbonate. Sufficient base, such as the alkali, is used to maintain the pH below 4.0 during the cyclization, for example from about 0.5 to 4.0, preferably from 0.5 to 2.5.

Among other factors, the present invention is based on my finding that surprisingly high yields of alpha-bromo-gamma-butyrolactone (BBL) are obtained if 2,4-dibromobutyric acid (DBBA) is cyclized using a base, preferably an alkali such as sodium carbonate, in accordance with the present invention. As mentioned above, I have found that cyclization reaction zone temperatures between about 45° and 65° C. are especially advantageous in obtaining fast reaction rates while still obtaining high yields in the present process. Also, maintaining the pH below 4.0 is especially advantageous in obtaining consistently high yields in the present process for cyclization of DBBA.

Suitable bases for the process of the present invention include ammonia, organic amines such as triethylamine, and other bases such as alkali hydroxide or carbonates. In using these bases it is critical to control the pH below 4.0.

The alkali used in the process of the present invention may be an alkali earth, that is, Ca or Ba; or an alkali metal, that is, Li, Na, K, Rb, or Cs. I have found the more mild bases such as the alkali metal and alkali earth carbonates, especially sodium carbonate and calcium carbonate, to be preferable in terms of consistency and reliability of high yields.

In the embodiment of the present invention wherein an overall process is provided for producing BBL, the feed to the first step is gamma-butyrolactone, bromine, and catalyst. Temperatures for the first step can be up to 180° C. or in a preferred alternate, maintained between 75° and 95° C.

The higher temperature of up to 180° C. for the 2,4-dibromobutyric acid (DBBA) formation step is found to be particularly applicable where the DBBA is formed in a closed, that is pressure vessel, reactor. When the reaction is carried out batch-wise, pressure for this first step may rise to about 150 to 200 psig due to the exotherm of the reaction, and temperatures may rise to 150°-200° C. When the reaction is carried out continuously, pressure and temperature may be maintained between 75° and 180° C. and pressure between 10 and 200 psig, for example, about 110° C. and 50 psig.

If the DBBA formation reaction is carried out in an "open" or non-pressurized system, temperatures of 75° to 95° C. are preferred.

Preferred feed amounts to the reaction zone for producing the 2,4-dibromobutyric acid are, based on 1 mol of the lactone feed, about 1.0 to 1.2 mols bromine and 0.03 to 0.07, more preferably 0.04 to 0.06, mol of the phosphorus halide catalyst. Residence time for the reaction preferably is 0.25 to 2.5 hours, more preferably 0.5 to 2.0 hours.

In the overall process embodiment, preferably the reaction mixture containing the resultant DBBA from the first step is passed to cyclization without separation of the DBBA.

Alternatively, the reaction mixture from the first step can be quenched with water and, if desired, an aqueous phase containing most of the hydrogen halide acid can be phase separated from the DBBA prior to feeding the DBBA to the cyclization step. In such an aqueous phase is separated, the preferred amount of base, preferably alkali metal carbonate, fed to the cyclization zone is about 0.5 to 0.75, more preferably 0.5 to 0.6, mols per mol DBBA. If such phase separation is not carried out, preferred amounts of alkali metal carbonate are about 0.55 to 0.85, more preferably 0.55 to 0.7, mols per mol of DBBA.

Preferred temperatures for the cyclization are between 20° and 90° C., more preferably between 30° and 80° C., most preferably about 45° to 65° C. Preferred pressures are between 10 and 200 psia, preferably about atmospheric pressure.

The cyclization reaction may be carried out in the absence of an added solvent or in the presence of a solvent.

Preferred solvents for the cyclization reaction are toluene, methylene dichloride and other hydrocarbons, halogenated hydrocarbons, etc., which are substantially inert organic solvents under the reaction conditions. The solvent should be an inert organic solvent. Toluene and methylene dichloride are preferred solvents for this purpose. The BBL resulting from the cyclization may be purified by stripping off the solvent or used in the solvent for subsequent chemical reaction.

Reference wwas made earlier to the use of the alpha-bromo-gamma-butyrolactones prepared as described herein as intermediates for the preparation of fungicides such as those disclosed in Chan, U.S. Pat. No. 3,933,860. An advantageous embodiment of the present invention is one wherein "straight-through" type processing is used to produce fungicidally active compounds such as those described in U.S. Pat. No. 3,933,860 and those described in Chan, U.S. Pat. No. 4,107,323. In this straight-through process, an inert organic solvent, toluene being especially preferred as a solvent in this regard is used straight through from the BBL formation step through the alkylation step and the acylation step. The alkylation step comprises reaction of the BBL or other similar lactone moiety with dimethylaniline or other similar aniline reactant. Preferred conditions for this alkylation reaction in the presence of an organic solvent such as toluene are described in the commonly assigned application of R. N. Reynolds entitled "Alkylation of Aniline with a Lactone in the Presence of Water", Ser. No. 847,503 filed Nov. 1, 1977. Preferred reaction conditions for the acylation step in the presence of a toluene solvent are described in the aforementioned Chan patents, and especially those acylation reaction conditions as described in the commonly assigned application of Reynolds, Ziman and Chan entitled "Acylation of a Lactone-Substituted Aniline Compound in the Absence of an Acid Acceptor", Ser. No. 847,504 filed Nov. 1, 1977.

EXAMPLES 1-21

Table I below summarizes results of several experiments run in an "open" system at atmospheric pressure, and also data from two literature references, namely the Plieninger and the Livak et al references previously cited. The mols catalyst and bromine in Table I are on a basis of 1 mol of gamma-butyrolactone feed.

Referring to Examples 1 and 2 (set A) in Table I, a Plieninger-type procedure was followed wherein 0.38 mol phosphorus catalyst was used per mol of the lactone. Bromine was added, in the amount of 2 mols per mol of lactone, stepwise with 1 mol being added at 25° C. and the second mol at 88° C. The reaction proceeds in two steps. In the first step 2,4-dibromobutyric acid (DBBA) is produced. The DBBA was converted to the product lactone either by heating with water at 100° C. (Example 1) or distilling under vacuum at 130°-140° C. (Example 2).

Examples 3, 4, 5, and 6, which are grouped together in set B, compared to Examples 10 and 11 in set D, illustrate the advantage I found in reducing catalyst levels for DBBA formation and using sodium carbonate as a base for the cyclization of DBBA compared to the prior methods of refluxing with water or thermal cracking. The results using sodium carbonate as given in Examples 3 through 6 show yields ranging from 80.9 to 88 mol percent, whereas the yields in Examples 10 and 11, wherein sodium hydroxide was used to facilitate the cyclization reaction, had a yield of only 33.8 to 34%.

Further in this regard, Examples 12 through 21 can be compared to Examples 10 and 11. These examples used sodium carbonate in the cyclization and achieved a much higher yield of BBL than was achieved in Examples 10 and 11, wherein sodium hydroxide was used. However, I believe that relatively high yields with sodium hydroxide may be obtained if the pH is carefully controlled to below 4.0.

Examples 3 through 19 are illustrative of the present invention, especially Examples 14, 17, 18 and 19. As indicated above, Examples 10 and 11 are not preferred embodiments of the present invention.

In Example 14, after 1 mol of the butyrolactone and 0.05 mol of the phosphorus tribromide catalyst were fed to the reaction zone, 0.60 mol of bromine was added at 25° C. and then an additional 0.60 mol of bromine was added at a temperature of slightly above 80° C. The time to form DBBA was 1 hour. This may be contrasted to Example 20, wherein using a higher temperature of about 100° to 130° C. and a catalyst of about 0.02 mol phosphorus tribromide a reaction time of about 14 hours was required to form the acid. Examples 20 and 21 respectively are tabulations of data from Livak et al as reported in the cited JACS article and in U.S. Pat. No. 2,530,348.

Referring again to Example 14, the data in the cyclization solvent column indicates in tabular form that the formation of BBL from the DBBA was carried out in a methylene dichloride solvent, which was added to the acid product resulting from the 1-hour acid-formation step. As indicated in Table I, the mol percent yield of BBL from the cyclization was 83.1% and the BBL assayed 96.6% purity. The temperature for the cyclization reaction was about 25° C. and the reaction time was about 3 hours, which is similar to other cyclization reaction temperatures and times for Examples 3 through 20.

EXAMPLE 22

In this example, a closed-system experiment was conducted under pressure. One mol of alpha-bromo-butyrolactone and 0.05 mol of phosphorus trichloride were charged to a Fisher-Porter glass vessel. Then 1.05 mol of bromine was added while keeping the vessel in contact with an ice bath so as to maintain the temperature about 5° to 30° C. Essentially no reaction took place during this time.

Then the vessel was put in a water bath maintained at about 80° to 85° C. After about 10 to 15 minutes, a sharp pressure increase was noticed, with pressure going from about 20 to 170 psig. Less than a minute later, the pressure began dropping rapidly, and the dense red color in the glass reactor was seen to dissipate as the solution cleared. This clearing of the solution is believed to mark the substantial completion of the reaction to form DBBA. The time elapsed from when the glass reactor was placed in the 80°-85° C. water bath was about 30 minutes.

Next, the reaction vessel was vented and 5 ml water was added at 80°-85° C. producing vigorous hydrogen bromide evolution. Then 50 ml of toluene was added to the contents of the glass reactor and the temperature adjusted to 50° C. Aqueous sodium carbonate in an amount of about 0.61 mol in 200 ml of water was added to the glass reactor while the temperaure was at about 50° to 60° C. The contents were stirred for about 15 minutes and then phase-separated to thereby separate an organic phase of BBL in toluene.

The aqueous portion from the phase separation was extracted twice with 50 ml of toluene to recover about 3 or 4% additional BBL in toluene. The over-all yield of BBL in toluene was about 85%.

EXAMPLE 23

In this example BBL was produced in a cyclization reaction carried out neat, that is, without an added organic solvent.

DBBA was first produced as follows: after 1.0 mol of butyrolactone and 0.05 mol of phosphorus trichloride was mixed at room temperature, the temperature was increased to 50° C. and 0.05 mol of bromine was added. An exotherm to 65° C. occured, after which the temperature was increased to 80° C. and 1.0 mol bromine was added over 12 minutes within a temperature range of 80°-100° C. After the bromine addition was complete, the reaction mixture was heated and maintained at 95° C. for two hours. The reaction mixture was then cooled to 80° C. and 5 ml of water was added producing vigorous hydrogen halide evolution.

The reaction mixture containing DBBA produced as described above was cooled to 50° C. and 0.61 mol of sodium carbonate in 195 ml of water was added over a 10 minute period. The reaction temperature was maintained between 50° and 60° C. for 15 minutes following the addition. The organic layer was separated and was found to contain 152 grams, 89.8 weight percent assay, 0.828 mol of BBL. The aqueous layer was extracted twice with dichloromethane. Removal of the dichloromethane solvent gave an additional 9 grams, 97.9 weight percent assay, 0.053 mol of BBL. The combined yield of BBL was 88.1 percent based on the butyrolactone feed.

EXAMPLE 24 (6475-45)

In this example bromine was added to butyrolactone and phosphorus trichloride as in Example 23. After bromine addition was complete the reaction was heated and maintained at 95° C. for two hours. The reaction mixture was then cooled to 50° C. and 37 ml of one molar aqueous sodium sulfite solution was added to destroy unreacted bromine.

The temperature of the mixture was adjusted to 50° C. and 24.3% aqueous sodium carbonate solution was added over a period of one hour with the rate of sodium carbonate additive adjusted to maintain the maximum pH equal to or below 2.5 during the addition. The temperature was maintained between 50° and 60° C. during this period. A total of 0.56 moles of sodium carbonate was required during the one hour period with eighty-five percent being added during the first four minutes.

After the one hour period, the organic layer was separated and was found to contain 152 grams, 93.4 weight percent assay, 0.798 mol of BBL. The aqueous layer was extracted twice with dichloromethane. Removal of dichloromethane solvent gave an additional 13.5 grams, 94.6 weight percent assay, 0.077 mol of BBL. The combined yield of BBL was 85.7 percent based on the butyrolactone feed.

The use of pH above and equal to 4.0 has been found in our work to result in inconsistent yields. For example, erratically lower cyclization yields have been obtained at pHs of 4, 7 and 9. However, I have found that adjusting the rate and/or amount of base, preferably alkali metal carbonate, addition to the cyclization reaction zone to control the pH below about 4.0 is effective to achieve consistent high yields in the process of the present invention.

TABLE I

| Experiment | Catalyst | Catalyst, Mols | Bromine: Mols Temp, °C. | Acid Formation, Hrs. | Cyclization Sol. | Cyclization Temp, °C. | Cyclization Time, Hrs | Bbl Yield, Mol % | Assay, Mol % | Comments |
|---|---|---|---|---|---|---|---|---|---|---|
| (1) (A) | 5970-26 P | 0.38 | 1 + 1 = 2  25°  >80° | 1.75 | H$_2$O | 100 | 1 | 71.8 | 95.8 | Plieninger procedure |
| (2) | -27 P | 0.38 | 1 + 1 = 2  25°  >80° | 1.75 | None Distil. | — | — | 81.6 | 88.4 | Plieninger procedure Thermal cracking of 2,4-DBBA. |
| (3) | -29 p | 0.39 | 1 + 1 = 2  25°  >80° | 1.0 | Benzene | 23 | 16$^a$ | 88.0 | 94.9 | This and experiments in sets C, E, F, G and H use Na$_2$CO$_3$ to cyclize with improved yields |
| (4) (B) | -30 P | 0.17 | 1 + 1 = 2  25°  >80° | 1+ | Benzene | 23 | 16$^a$ | 86 | 96.5 | |
| (5) | -31 P | 0.086 | 1 + 1 = 2  25°  >80° | 1+ | Benzene | 23 | 16$^a$ | 80.9 | 93.8 | |
| (6) | -34 P | 0.043 | 1 + 1 = 2  25°  >80° | 1+ | Benzene | 23 | 3 | 83.6 | 96.2 | |
| (7) (C) | -35 P | 0.086 | 1 + 0.4  25-80°  >80° | 1.5 | Benzene | 23 | 2 | 73.4 | 93.2 | |
| (8) | -36 P | 0.043 | 1.14  <80° | 1.5 | Benzene | 23 | 16$^a$ | 71.4 | 87.3 | All bromine added <80° Reaction heated to 80-85° C. and maintained. |
| (9) | -37 P | 0.01 | 1.03 <80° | 4 | Benzene | 23 | 16$^a$ | 73.3 | 91.4 | |
| (10) (D) | -38 P | 0.088 | 1.46 <80° | 1 | Benzene | 23 | 16$^a$ | 34 | 93.4 | NaOH used as base. |
| (11) | -39 P | 0.88 | 1.46 <80° | 1 | CH$_2$Cl$_2$ | 23 | 16$^a$ | 33.8 | 91.3 | NaOH used as base. |

TABLE I-continued

| Experiment | | Catalyst | Catalyst, Mols | Bromine: Mols Temp. °C. | Acid Formation, Hrs. | Cyclization Sol. | Cyclization Temp. °C. | Cyclization Time, Hrs | Bbl Yield. Mol % | Assay, Mol % | Comments |
|---|---|---|---|---|---|---|---|---|---|---|---|
| (12) (E) | -40 | PBr₃ | 0.05 | 1.14 <80° | 2 | Benzene | 23 | 1 | 79.6 | 94.3 | |
| (13) | -42 | PBr₃ | 0.05 | 1.2 70–80° | 3 | CH₂Cl₂ | 23 | 3 | 77.6 | 93.3 | |
| (14) (F) | 5970-43 | PBr₃ | 0.05 | 0.6 + 0.6 25° >80° | 1 | CH₂Cl₂ | 23 | 16ᵃ | 83.1 | 96.6 | |
| (15) | -44 | PBr₃ | 0.02 | 1.2 >80° | 3 | CH₂Cl₂ | 23 | 5 | 86 | 98.0 | |
| (16) | -46 | PBr₃ | 0.01 | 0.04 + 0.63 25° >80° | 5.5 | | 23 | 4 | 83.1 | 95.8 | |
| (17) (G) | -48 | PBr₃ | 0.05 | 0.6 + 0.6 25° >80° | 1 | Neat | 23 | 16ᵃ | 77.6 | 93.9 | |
| (18) (H) | -49 | PCl₃ | 0.05 | 0.6 + 0.6 25° >80° | 1+ | CH₂Cl₂ | 23 | 16ᵃ | 84.6 | 97.2 | |
| (19) | 6024-8 | PCl₃ | 0.05 | 0.6 + 0.6 25° >80° | 1.5 | Neat | 23 | 16ᵃ | 76.4 | 92.6 | |
| (20) (I) | | PBr₃ | 0.02 | 0.95 100–130° | 14 | Neat | 130 | 4 | 82 | N.A. | Livak et al; JACS 67, 2218 (1945). Distillation required. |
| (21) | | PBr₃ | 0.02 | 1.0 120–130° | 6.5 | Neat | N.A. | N.A. | 85 | N.A. | USP 2,530,348 |
| (22) | 6054-42 | PCl₃ | 0.05 | 1.05 80° Bathᵇ | <1 | Toluene | 50° | 0.25 | 86.5 | 91.3 | Sealed reactor, P_max = 170 psig for DBBA reaction. |
| (23) | 6254-46 | PCl₃ | 0.05 | 0.05 + 1.0 >50° >80° | 1 | Neat | 50° | 0.25 | 88.1 | 89 | |
| (24) | 6475-45 | PCl₃ | 0.05 | 0.05 + 1.0 >50° >80° | 2 | Neat | 50° | 1.0 | 85.7 | 94 | |

ᵃStirred overnight.
ᵇBut exotherm briefly raised reaction temperature to about 170° C. during DBBA formation.

What is claimed is:

1. A process for cyclizing 2,4-dibromobutyric acid to alpha-bromo-gamma-butyrolactone which comprises contacting the dibromobutyric acid with an alkali metal carbonate in a reaction zone at a temperature between 20° C. and 100° C. wherein sufficient of said alkali metal carbonate is added to the reaction zone to maintain a pH between 0.1 and 4.0 in the reaction zone during the cyclization.

2. A process in accordance with claim 1 wherein the temperature is 30° to 80° C.

3. A process in accordance with claim 1 wherein the alkali metal carbonate is sodium carbonate.

4. A process in accordance with claim 2 wherein the alkali metal carbonate is sodium carbonate.

5. A process in accordance with claim 4 wherein sufficient of the sodium carbonate is added to the reaction zone to maintain the pH between 0.5 and 2.5 during the cyclization reaction.

6. A process for making alpha-bromo-gamma-butyrolactone which comprises: feeding to a reaction zone butyrolactone, bromine and a phosphorus halide catalyst in a mol ratio of about 1 mol of the lactone, 0.5 to 1.2 mols of bromine, and 0.01 to 0.10 mol of the catalyst; contacting the lactone, bromine and phosphorus halide in the reaction zone at a temperature between 75° and 180° C. to thereby form 2,4-dibromobutyric acid; and cyclizing the dibromobutyric acid by contacting it at a pH between 0.1 and 4.0 with an alkali metal carbonate at a temperature between 10° and 90° C. to thereby obtain alpha-bromo-gamma-butyrolactone.

7. A process in accordance with claim 6 wherein the 2,4-dibromobutyric acid is dissolved in an inert organic solvent before the cyclizing step.

8. A process in accordance with claim 7 wherein the organic solvent is toluene.

9. A process in accordance with claim 7 wherein the alkali metal carbonate is sodium carbonate and sufficient of the alkali is added to the reaction zone to maintain the pH from 0.5 to 2.5 during the cyclizing reaction.

* * * * *